United States Patent

Mastico et al.

[11] Patent Number: 5,698,424
[45] Date of Patent: Dec. 16, 1997

[54] CAPSID FORMING AND CYSTEIN MODIFIED CHIMAERIC MS2-COAT PROTEIN

[75] Inventors: Robert Allan Mastico, Braintree, Mass.; Peter George Stockley, Ilkley, England

[73] Assignee: British Technology Group Ltd., England

[21] Appl. No.: 167,982

[22] PCT Filed: Jun. 26, 1992

[86] PCT No.: PCT/GB92/01159

§ 371 Date: Jan. 3, 1995

§ 102(e) Date: Jan. 3, 1995

[87] PCT Pub. No.: WO93/00434

PCT Pub. Date: Jan. 7, 1993

[30] Foreign Application Priority Data

Jun. 28, 1991 [GB] United Kingdom ............... 9114003

[51] Int. Cl.⁶ .................. C12N 15/11; A61K 35/76
[52] U.S. Cl. .............. 435/172.3; 435/69.3; 435/320.1; 424/186.1; 424/193.1; 424/194.1; 536/23.72
[58] Field of Search .................... 424/186.1, 193.1, 424/194.1, 196.11, 201.1, 202.1, 204.1; 435/69.1, 7, 172.1, 252.3, 252.33, 320.1, 69.3, 172.3; 536/23.72

[56] References Cited

FOREIGN PATENT DOCUMENTS

WO9213081  8/1992  WIPO.

OTHER PUBLICATIONS

Fieb et al. Nature 1976 vol. 260:500–507.
Peabody J. Biol. Chem 5 Apr. 1990 vol. 265 No. 10 5684–5689.
Reisner et al Thrombosis & Haemastasis vol. 58 No. 1 p. 58 1987.
Rohrmann et al. Biochem Biophys Res Com. 1970 vol. 38 No. 3: 406–413.
Y.M. Berzin et al, Biological Abstracts vol. 74 (1982) Abstract No. 51034.

*Primary Examiner*—Lila Feisee
*Assistant Examiner*—Julie E. Reeves
*Attorney, Agent, or Firm*—Graham & James LLP

[57] ABSTRACT

A chimaeric protein is provided, capable of forming part of a capsid assembly and comprising the amino acid sequence of the coat protein of phage MS-2, or a conservatively modified variant thereof, or sufficient of said sequence or variant to retain the capability of forming a capsid assembly, which amino acid sequence has been modified by removal of the cysteine residues present externally of the N-terminal protruberant β-hairpin of the coat protein and insertion of a cysteine residue within the region corresponding to the N-terminal protruberant β-hairpin.

16 Claims, 2 Drawing Sheets

CAPSID FORMING AND CYSTEIN MODIFIED CHIMAERIC MS2-COAT PROTEIN

This application claims priority under 35 USC 371 from International Application PCT/GB92/01159, filed Jun. 26, 1992 and priority under 35 USC 119 from United Kingdom Application 9114003.8, filed Jun. 28, 1991.

This invention relates to a chimaeric protein and particularly directed to virus proteins containing foreign inserts, the preparation of such proteins and their use, for example as vaccines or as carriers for presenting molecular species such as targeting moieties.

BRIEF DESCRIPTION OF THE DRAWINGS

The present invention is illustrated by the accompanying drawings, in which.

Figure 1:
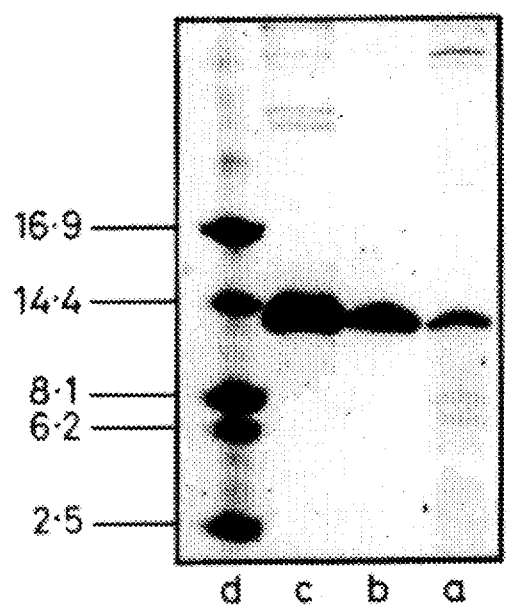
FIG. 1 is an SDS-PAGE tracing of MS2 capsid proteins.

Epitopes inserted insertion in an identified class of virus protein carriers can be specifically directed so that foreign epitopes are reliably presented on the surface of the protein capsid assembly after the expression of the chimaeric protein in a bacterial host.

It was by no means predictable that such a result could be achieved. Not all viruses possess coat proteins which will self assemble: furthermore it is not possible to predict such self assembly. Even further, unlike animal viruses, bacterial viruses cannot naturally be expected to possess immunodominant regions and there is thus no guidance as to which region of a bacterial virus coat protein (if any) could be modified in the reasonable expectation of inducing an immune response.

One example of a chimeric protein is capable of forming part of a capsid assembly and comprises the amino acid sequence of the coat protein of phage MS-2, or a conservatively modified variant thereof, or sufficient of said sequence or variant to retain capsid-forming capability, which amino acid sequence has been modified by insertion of a foreign epitope in the region of the protein corresponding to an N-terminal β-hairpin, as determined by X-ray crystallography of the whole phage particle.

Surprisingly, it was found that such a chimaeric protein can be expressed in a suitable bacterial host to yield capsids empty of the phage RNA and largely free of other nucleic acid contaminants.

While it is contemplated that the Insertion of a foreign epitope which is a linear polypeptide of comparatively short length, for example up to about 30 amino acid residues, can be accomplished, it will be appreciated that the presentation of non-linear epitopes by simple insertion in the β-hairpin may not be feasible. Thus many epitopes do not consist of simple linear fragments of polypeptide: instead they are made up of several such fragments spatially related by the overall three-dimensional folding of the native protein antigen, i.e. discontinuous epitopes. It is clearly desirable to be able to present such epitopes at the surface of the phage capsid.

It has now been found that the coat protein of MS-2 can be employed with a view to presenting a range of epitopes or other molecular species such as targeting moieties at the capsid surface by removing the cysteine residues which occur at sites not included within the N-terminal β-hairpin and introducing a cysteine residue within the β-hairpin region, which cysteine residue is then available for linking with desired antigens or other molecular species, suitably via an appropriate spacer.

Therefore in accordance with the present invention there is provided a chimaeric protein capable of forming part of a capsid assembly and comprising the amino acid sequence of the coat protein of phage MS-2, or a conservatively modified variant thereof, or sufficient of said sequence or variant to retain the capability of forming a capsid assembly, which amino acid sequence has been modified by removal of the cysteine residues present externally of the N-terminal protruberant β-hairpin of the coat protein and insertion of a cysteine residue within the region corresponding to the N-terminal protruberant β-hairpin.

The cysteine residues external to the β-hairpin are suitably removed by mutation at the appropriate sites of the coat protein cDNA.

The inserted cysteine may be linked directly to a desired molecular species to be presented such as an epitope, especially a non-linear antigenic protein, or to other molecular species to be presented such as a targeting moiety. Alternatively, a spacer moiety may be employed between the cysteine and the molecular species to be presented, thus extending the range of species that can be presented.

Suitable spacer moieties are selected from known commercially available heterobifunctional crosslinking reagents which couple with the exposed cysteine thiol group. Examples of such cross-linkers are m-maleimidobenzoyl-N-hydroxy-sulfosuccinimide ester, N-succinimidyl-(4-iodoacetyl)aminobenzoate and N-succinimidyl-3-(2-pyridyldithio)propionate. The choice of crosslinker will depend on the molecular species to be presented and its size. Thus larger molecular species may require longer crosslinking moieties to minimize steric hindrance. The crosslinker may be linked first to the cysteine residue or first to the molecular species to be presented.

The chimaeric coat protein is preferably that derived from phage MS-2, but it may also be derived from related RNA-phages capable of replication in E. coli, such as phages R17, fr, GA, Qβ and SP. Such RNA-phages of physical structure similar to that of MS-2 will contain some chemical variation in the amino acid residues of the coat protein and are thus conservatively modified variants of MS-2 coat protein. While it is believed at present that substantially the entire coat protein may be required for capsid assembly, deletions and/or insertions of a relatively minor nature may also be possible whilst still retaining capsid-forming capability. Proteins having such modified sequences are included within the scope of the invention.

As stated above, the foreign moiety is inserted at the region of the protein which in the assembled capsid corresponds to the N-terminal β-hairpin. The three-dimensional structure of the MS-2 phage particle has been published by Valegard et al., (Nature, 1990, 345, 36–41). The published data show that, firstly, the structure of the coat protein is not related to the eight-stranded β-barrel motif found in all other spherical RNA virus subunits whose structures are known at the present time. Secondly, although the coat protein exhibits quasi-equivalent inter-subunit contacts, there are no other devices, such as extended arms of polypeptide, helping to secure each protein conformer. The coat protein structure can be viewed in terms of three separate regions. These are not domains in the usual sense but could represent independent folding units. These regions are residues 1–20, which form the β-hairpin structure which protrudes from the surface of the phage forming the most distal radial feature. This region is followed by residues 21–94 which form five β-strands including the "FG-loop" which is the site of the only major conformational change between quasi-equivalent conformers. These β-strands are then followed by two α-helices, residues 95–125, which interdigitate to secure dimers of the coat protein sub-units. Valegard et al. are concerned solely with the physical structure of the MS-2 virus and do not attempt to elucidate the mode of action of the virus.

As explained above, the present invention comprises modification of the coat protein amino acid sequence by introduction of a cysteine residue in the region corresponding to the protruberant hairpin. The chimaeric protein of the invention has therefore been so modified in the region of amino acid residues 1 to 20, such numbering being with reference to the entire coat protein sequence of MS-2 as published by Fiers, Nature, 1976, 260, 500–507. Preferably the modification to introduce the cysteine residue is towards or at the middle of the hairpin region. It is preferred to introduce the cysteine in the region of the glycine 13 and 14 of the coat protein. The cysteine residues to be removed which are external of the β-hairpin are found at positions 46 and 101. They may be removed by any convenient conventional genetic engineering technique, suitably by site-specific mutagenesis.

In a preferred method of removing the unwanted cysteine residues, two mutants of the MS-2 coat protein, one singly mutated at cys 46 and one singly mutated at cys 101 may be obtained by standard commercially available techniques for site specific mutagenesis and the corresponding cDNA sequences introduced into standard expression vectors, which vectors are subjected to digestion with restriction enzymes to obtain separately the DNA fragment containing the mutated cys 46 site and the corresponding fragment containing the mutated cys 101 site, the fragments being subsequently ligated to give a doubly-mutated coat protein cDNA. The doubly-mutated cDNA may then be subjected to site-directed mutagenesis using standard methods to introduce a cysteine residue in the β-hairpin region.

There can be further linked to the introduced cysteine residue with or without interposition of a spacer moiety, a desired molecular species to be presented. Examples of such species are a 9-mer peptide sequence derived from the haemagglutinin of the human pathogen influenza virus (or a haemagglutinin moiety containing the epitope), or the IgE decapeptide described therein (which is also described and claimed In International Patent Application Publication No. WO90/15878). Further alternative species which may be linked to the cysteine residue include Foot and Mouth Disease Virus (FMDV) VPl, luteinizing hormone releasing hormone (LHRH) and HIV gp160 and 120 proteins, and enzymes such as horseradish peroxidase.

The invention also therefore extends to chimaeric proteins comprising such a foreign molecular species, and, optionally, a spacer, linked to a cysteine residue in the β-hairpin region of the coat protein. It will be appreciated that the foreign molecular species and optional spacer may be linked to the cysteine residue before or after capsid assembly. The invention further extends to capsid assemblies of the chimaeric proteins of the invention. It has been found that such capsids can be expressed in *E. coli* as "phage empties" without the RNA of the live virus. The generation of mixed capsid assemblies is contemplated, for example by prior disassembly of in vivo assembled samples followed by reassembly of a mixture. Such capsid assemblies are Intended, for example, to be capable of raising a mixed immune response and thus capable of finding application as vaccines for immunisation against a natural spectrum of vital epitopes in a population. The invention therefore also extends to vaccines comprising one or more chimaeric proteins as defined above.

The chimaeric proteins and assembled capsids of the present invention are envisaged for employment for example as vaccines.

In addition, they are envisaged for employment for targeting, for example by addition of a galactose residue, which would direct the capsid to interact with specific cell surface receptors. Such targeting techniques may be useful in the carrying of foreign moieties to and into specific cells. Foreign moieties may be initially held by encapsidation within the coat protein capsids filed concurrently herewith. Such foreign moieties may include genes, ribozymes, antisense messages or cytotoxic agents.

It will be apparent that there are several advantages in using MS-2 and related phages as a presentation system. Thus the empty coat protein capsids can be readily expressed in comparatively high yield in *E. coli*, the product is easily purified and it has been found that the assembled capsids show considerable stability with respect to a range of temperatures, pH and ionic strength. While not wishing to be bound by any particular theory, it is postulated that the invention also allows one to present molecular species such as epitopes in a regular array on the surface of carrier capsids, at predetermined locations, which will maximise immune recognition, which relies on the multidentate nature of antibody molecules. The possibility also arises of maintaining the three dimensional structure of the epitope or other species being introduced.

It is believed that the MS-2 system has considerable potential utility for the presentation of foreign molecular species on the surface of a spherical bacteriophage. The system has a number of advantages over the filamentous bacteriophage alternatives. The MS-2 coat protein is capable of facile self-assembly in the absence of nucleic acid unlike the filamentous phages in which assembly is concomitent with encapsidation of nucleic acid. Furthermore, the filamentous coat protein must undergo a post translational processing and membrane insertion before assembly occurs whereas the MS-2 protein is unprocessed. The MS-2 system also has the advantage of a detailed molecular model for the coat protein allowing the effects of foreign peptide insertion to be modelled.

The following specific description illustrates the invention by way of example.

A) Isolation of single mutant MS-2 coat protein genes.

Site directed mutagenesis and standard techniques were used to produce amino acid mutants at coat protein positions 46 and 101.

Mutants were selected having either cysteine at position 46 substituted by serene or cysteine at position 101 substituted by serine.

Each single mutant DNA was expressed in *E. coli* to demonstrate the ability to self assemble.

B) Preparation of doubly mutated cDNA.

The ser 46 single mutant from step A) was introduced into standard coat protein expression vector pTAC-CP and digested with SacI and XbaI restriction enzymes and the longer backbone fragment so obtained treated with calf intestinal phosphatase and then purified on agarose or polyacrylamide gels before electroelution and precipitation.

The ser 101 mutant from step A) was treated likewise with omission of the phosphatase treatment. The smaller fragment containing the C-terminal portion of the coat protein gene was purified by gel electrophoresis.

The large fragment containing the mutated cys 46 site and the small fragment containing a mutated 101 site were ligated by standard methods. The recombinant molecules thus obtained were used to transform *E. coli* TG1 to ampicillin-resistance and positive colonies checked for double mutation by DNA sequencing.

C) Introduction of cysteine residue.

The doubly-mutant ser 46/101 coat protein cDNA from step B was introduced into an M 13 sequencing vector by standard subcloning methods, a single stranded template for site-directed mutagenesis generated and a cysteine residue introduced at gly 14 using the commercially available site specific mutagenesis protocol based on nucleotide phosphothioates. There was thus obtained mutated cys 14 Ser 46/101 coat protein cDNA.

D) Protein production and purification.

The isolated mutated cDNA was expressed in *E. coli* to confirm the capsid-forming ability of the recombinant protein. The cys 114 set 46/101 coat protein cDNA of C) above was introduced into the expression vector pTAC-CP and the resultant plasmid used to transform *E. coli* strain TG1 to ampicillin resistance. Chimaeric proteins were expressed in accordance with the following procedure.

5×5 ml (2TY media with 100 μg/ml ampicillin) cultures of single colonies picked from transformation plates were grown for approx. 4 hrs at 37° C. and then used to inoculate 5×500 ml flasks of 2TY plus ampicillin and the cultures were grown at 30° C. When the cultures reached $OD_{600}$ approx. 0.45 protein production was induced by adding 1 mM isopropyl-1β-D-thio-galactoside (IPTG). Cells grown overnight were then centrifuged at 3 k rpm, 30 mins, 4° C. in a Beckman JA14 rotor.

The resulting pellets were resuspended in 50 mM Hepes, 100 mM NaCl, 10 mM dithiothreitol (DTT), 5 mM EDTA and 1 mM phenyl methyl sulphonyl fluoride (PMSF) and the cells lysed by sonication. The cell lysate was then centrifuged at 15k, 20 mins, 4° C. in a Beckman JA20 rotor and the supernatant passed down a NAP-25 column (Pharmacia) to change buffers to 20 mM NaPi (sodium phosphate-based buffer) pH 7.0. 1 ml fractions were collected from the NAP column, the MS-2 coat protein containing fractions (nos. 2 to 5 inclusive) added to an anti-MS-2 coat protein immunoaffinity column and the sample allowed to bind for 1 hour at room temperature with gentle agitation.

The column was washed with 20 mM NaPi pH 7, then 10 mM NaPi/100 mM NaCl pH 7. The sample was eluted with 20 mls 20 mM acetic acid/200 mM NaCl approx. pH 2.7 and the first 4 mls collected.

The pH was immediately adjusted by titration with 1M Tris.HCl pH 9 to pH 7–7.4 and the mixture centrifuged at 30k rpm, 4° C. overnight (approx. 15 hrs) using a Beckman SW.55Ti rotor. The supernatant was decanted and the MS-2 protein pellet resuspended in a small volume of the required buffer.

Homogenous cys 14 modified capsids were obtained which were tested for their ability to react with an activated galactose reagent as described in E) below.

SDS-PAGE of the resultant immunoaffinity purified cys-14 modified capsids showed essentially a single component of the expected molecular weight. This result is shown in FIG. 1 where lane a) shows the cys-14 modified capsids, lanes b) and c) show wild type capsids respectively immunoaffinity purified and sucrose density purified and lane d) gives molecular weight standards.

Figure 2:
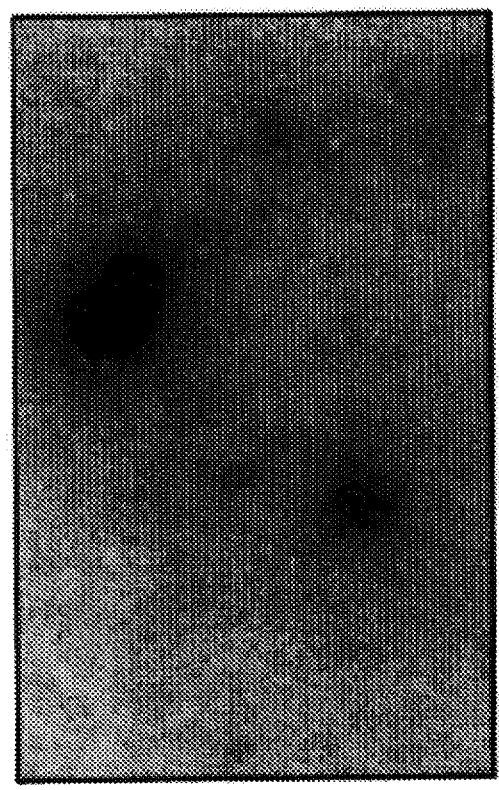
FIG. 2 is an electromicrograph of cys-14 modified capsids assembled into particles.

FIG. 2 shows an electromicrograph of the immunoaffinity purified cys-14 modified capsids showing the presence of assembled particles similar to those produced by wild type coat proteins.

E) Reaction of cys 14 modified protein with activated galactose.

In order to test the reactivity of the cys 14 modified MS-2 capsids, a halogen-activated galactose reagent was prepared as follows:

To a stirred solution of p-aminophenyl β-D-galactopyranoside (0.54 g; 2 mmole) in water (4 ml) and ethanol (6 ml) was added iodoacetic anhydride (0.9 g; 2.5 mmole) at room temperature. After 2 hours, the reaction was concentrated to dryness and the residue washed with ether (2×10 ml). Crystallisation from ethanol gave the product as needles (0.7 g; 80%), mp 158°–160° C.

Figure 3:
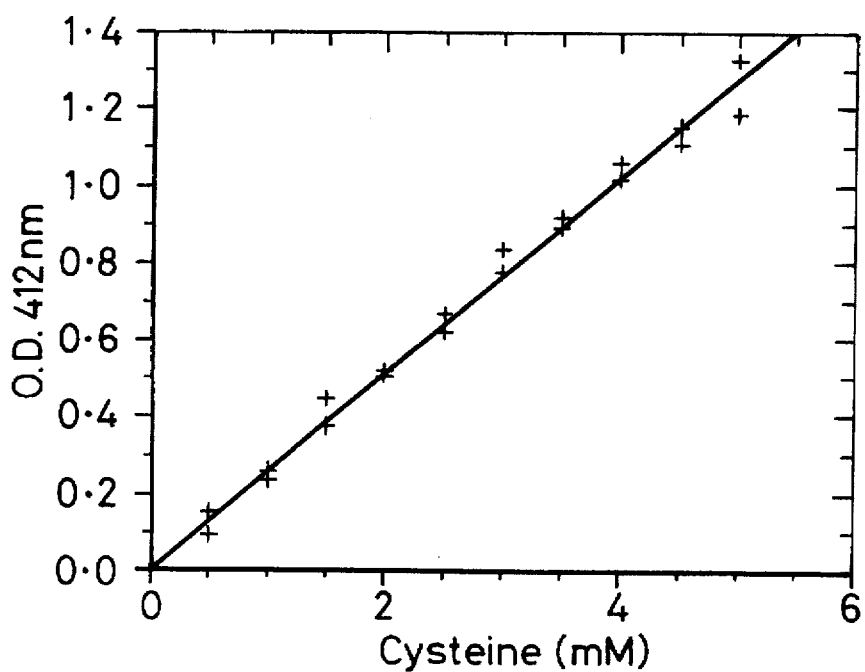
FIG. 3 is a graph used to determine the extent of reaction of free cysteine with Ellman's reagent.

The reaction of the cys 14 modified capsids with the activated galactose was assayed using Ellman's reagent (dithionitrobenzoate, DTNB) which gives a characteristic absorption at $OD_{412}$ on reaction with free —SH groups. FIG. 3 shows a control curve for reaction of free cysteine with DTNB. The control curve was obtained using:

100 μl sample.

100 μl DTNB 4 mg/ml in 100 mM $Na_2HPO_4$ pH8 ("buffer 1").

5 ml "buffer 1"

The mixture was left at room temperature for 15 mins after adding DTNB and then the $OD_{412}$ recorded.

Figure 4:
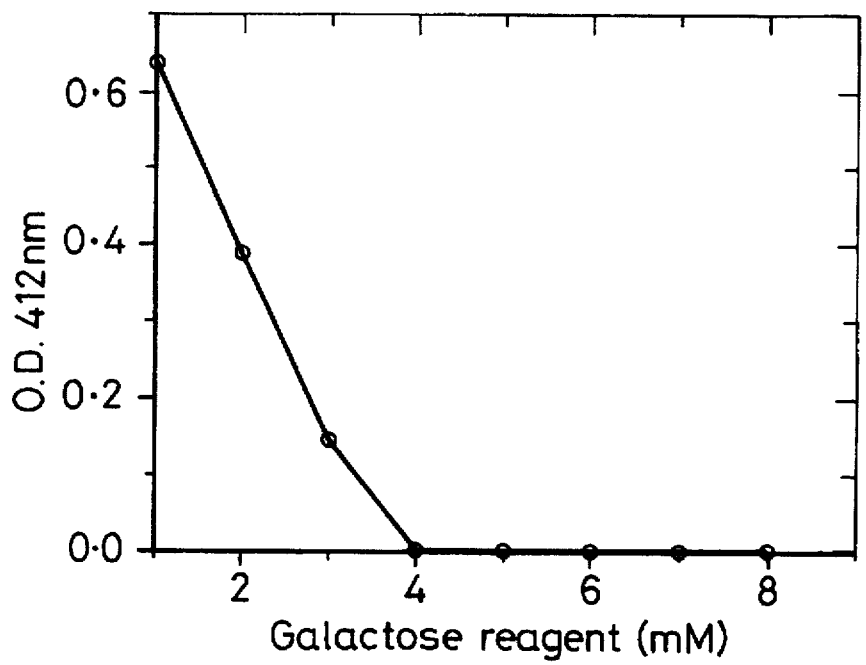
FIG. 4 is a graph showing the reaction of cysteine and activated galactose.

FIG. 4 shows the curve obtained when cysteine (4 mM) was mixed with from 1 to 10 mM activated galactose and left to stand at room temperature for 1 hour, followed by assay of 100 μl aliquots as described above using DTNB.

The cys 14 modified coat protein was reacted with DTNB as follows:

Purified cys 14 modified capsids were resuspended in buffer 1 containing 1 mM EDTA to a final concentration of 400 μg/ml. The following individual experiments were set up.

1) 100 μl protein sample, 100 μl 5 mM activated galactose.

2) 100 μl protein sample, 90 μl buffer 10 μl 5 mM activated galactose.

3) 100 μl protein sample, 100 μl buffer 1.

Each was left stirring at room temperature for 1 hour before addition of 200 μl DTNB 4 mg/ml in ethanol to the stirring solution. $OD_{412}$ was recorded after 15 mins and the results are shown in Table 1 below. The number of free thiols decreased with increasing exposure to the galactose reagent, confirming that the cys 14 capsids had been derivatised with galactose.

TABLE 1

| | Sample | $O.D._{412\,nm}$ |
|---|---|---|
| | Buffer blank | 0.0 |
| 1) | 100 μl MS2-cys; 100 μl gal | 0.031 |
| 2) | 100 μl MS2-cys; 90 μl buffer; 10 μl gal | 0.080 |
| 3) | 100 μl MS2-cys; 100 μl buffer | 0.118 |

F) Linking of cys 14 modified coat protein to immunogenic peptide.

The purified cys 14 modified capsids were linked as described below to HA10, a 10-mer peptide sequence encompassing a nonapeptide epitope derived from the haemagglutinin of the human pathogen influenza virus and having an N-terminal cysteine residue extension, which 9-mer sequence YPYDVPDYA SEQ ID NO: 1 has been identified as containing one of the antigenic determinants by Wilson et al., Molecular and Cell Biology, May 1988, 2159–2165 and Cell, 37, 1984, 767–778. The procedure involved an initial crosslinking step to form a disulphide linkage which was then oxidised.

The following reagents were employed to make up four test reaction mixtures:

2 μg cys 14 modified capsids (about 3 μl) ("cys bridge")
1 μl 1M Tris.HCl pH8, 10 mM EDTA ("buffer 2")
17 μg HA9 peptide (about 2 μl) ("peptide")
1 μl 2-mercaptoethanol ("βME")

The following four test mixtures were prepared, in each case made up to 10 μl with water:

1) cys bridge+buffer 2+βME
2) cys bridge+buffer 2
3) cys bridge+buffer 2+βME+peptide
4) cys bridge+buffer 2+peptide The mixtures were incubated for 1 hour at room temperature. There was then added 1 μl of a mixture of 0.37M sodium tetrathionate and 1.6M sodium sulphite (which had been freshly prepared in accordance with the method of Morehead et al., Biochem., 23, 1984, 2500). The mixtures were left overnight at room temperature.

The mixtures were analysed using a PAGE Schägger System (Schägger et al., 1987, Anal. Biochem., 166, 368–379), blotted onto nitrocellulose paper using a Bio-Rad Western blotting apparatus, with a transfer buffer of 39 mM glycine, 48 mM Tris, 0.1% (w/v) sodium dodecyl sulphate (SDS) and 20% methanol for a transfer time of 1 hour at 450 mA.

The blots were washed with phosphate buffered saline (PBS) pH 7.6 containing Tween 20 (polyoxyethylene sorbitan monolaurate –3 ml per liter PBS) to equilibrate. They were then incubated for 1 hour at 37° C. with 35ml PBS-Tween plus 0.5% (w/v) bovine serum albumin (BSA), washed 6×5 min. with 200 ml PBS-Tween and subsequently incubated overnight at 4° C. with 35 ml PBS-Tween +0.5% (w/v) BSA together with 100 μl mouse anti-HA9 monoclonal antibody (obtained from Balcore Co., Berkley, U.S.A.). There then followed washing with PBS-Tween (6×5 min.–200 ml) and incubation for half an hour with 35 ml PBS-Tween+0.5% (w/v) BSA together with 50 μl goat anti-mouse IgG horseradish peroxidase (HRP) conjugate. After further washing (6×6 min.–200 ml PBS-Tween), the gel was excited by luminol Western blotting reagents (Amersham) and visualised.

The results showed that only a single band in the lane corresponding to sample number 4 cross-reacted with the anti-HA9 antibody. This is the expected result, samples 1–3 being negative controls. Thus it is possible to couple linear peptide fragments to cys 14 capsids using these methods.

G) Covalent cross-linking of cys 14 modified coat protein to an enzyme.

The purified cys 14 modified capsids described in E) above were covalently linked via a maleimide group to the enzyme horseradish peroxidase (HRP) as follows:

HRP-maleimide conjugate (Pierce Europe BV, Holland), cys 14 modified capsids and βME were used to make the following mixtures, each of which was made up to 100 μl with 100 mM NaPi, pH 7.2:

1) 20 μg HRP-maleimide plus 1 μl βME
2) 20 μg cys 14 modified capsids plus 1μl βME
3) 20 μg cys 14 modified capsids plus 20 μg HRP-maleimide Sample 3) was left for 1 hour at room temperature and then βME added to quench any remaining thiols. Samples 1–3 were then fractionated by HPLC gel filtration chromatography on PW 3000, 2×30 cm columns, in 100 mM NaPi, pH 7.2 at a flow rate of 0.5 ml/min. Fractions (1 min. - 0.5 ml) of the eluate were than assayed for HRP activity using the commercially available kit (ABTS reagent, Pierce), enzyme activity being estimated by observing the increased absorbance of solutions at 410 nm. The data showed a significant increase over background levels in fractions corresponding to the $OD_{280}$ peak of cys 14 assembled material of sample 3.

We claim:

1. A modified coat protein capable of forming a capsid which comprises the coat protein of a bacteriophage selected from the group consisting of MS-2, R17 and fr, wherein the coat protein is modified by an insertion of a cysteine residue in the region of corresponding to glycine residue 13 and 14 of N-terminal β-hairpin region, and by replacement of each of the cysteine residues located external to the N-terminal β-hairpin region by a non-cysteine amino acid residue.

2. A modified coat protein capable of forming a capsid which comprises the coat protein of a bacteriophage selected from the group consisting of GA, Qβ and SP, wherein the coat protein is modified by an insertion of a cysteine residue in the region corresponding to glycine residue 13 and 14 of the N-terminal β-hairpin region when the bacteriophage is GA, or in the region of amino acid residues corresponding to glycine residue 13 and 14 of GA when the bacteriophage is Qβ or SP, and, when the coat protein contains cysteine residues external to the N-terminal β-hairpin region, the coat protein further modified by removal of each of the external cysteine residues.

3. The modified coat protein according to claim 1, wherein the bacteriophage is MS-2.

4. The modified coat protein according to claim 3, wherein the inserted cysteine residue replaces glycine 13 or 14 residue of the N-terminal β-hairpin region of the coat protein.

5. The modified coat protein according to claim 4, wherein each cysteine residue removed is replaced by a serine residue.

6. The modified coat protein of claim 1 further comprising a foreign molecular species linked to the inserted cysteine residue.

7. The modified coat protein of claim 6, wherein the foreign molecular species is linked to the inserted cysteine residue via a spacer moiety.

8. The modified coat protein of claim 7, wherein the spacer moiety is derived from a bifunctional crosslinking reagent selected from the group consisting of m-maleimidobenzoyl-N-hydroxysulfosuccinimide ester, N-succinimidyl-(4-iodoacetyl)aminobenzoate and N-succinimidyl-3-(2-pyridyldithio)propionate.

9. The modified coat protein of claim 6, wherein the foreign molecular species is an antigenic protein.

10. The modified coat protein of claim 6, wherein the foreign molecular species is a targeting moiety.

11. The modified coat protein of claim 10, wherein the targeting moiety comprises galactose.

12. A capsid formed by the modified coat protein of claim 1.

13. A capsid formed by the modified coat protein of claim 3.

14. A method of preparing a modified coat protein according to claim 3, the method comprising:

providing a first cDNA sequence encoding the coat protein of bacteriophage MS-2 from which the codon for cysteine 46 residue has been replaced with a non-cysteine amino acid residue;

providing a second cDNA sequence encoding the coat protein of bacteriophage MS-2 from which the codon for cysteine 101 residue has been replaced with a non-cysteine amino acid residue;

digesting the first cDNA sequence and the second cDNA sequence and ligating the digested cDNA sequences to produce a ligated cDNA sequence encoding the coat protein of bacteriophage MS-2 from which both the codon for cysteine 46 residue and the codon for cysteine 101 residue are removed;

subjecting the ligated coat protein cDNA sequence to site-directed mutagenesis to introduce a cysteine codon in the region of glycine residue 13 and 14 of the N-terminal β-hairpin region of ligated coat protein cDNA;

expressing the resulting cDNA in a host cell to obtain the modified coat protein.

15. The method of claim 14, wherein the host cell is *E. coli*.

16. An expression vector comprising DNA sequence encoding the modified protein of claim 1.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 9 AMINO ACIDS
( B ) TYPE: AMINO ACID
( D ) TOPOLOGY: Not Relevant ( i i ) MOLECULE TYPE: PEPTIDE ( x i ) SEQUENCE DESCRIPTION: SEQ ID NO: 1:

Tyr  Pro  Tyr  Asp  Val  Pro  Asp  Tyr  Ala
                        5                        9